(12) United States Patent
Stronks et al.

(10) Patent No.: US 10,441,500 B2
(45) Date of Patent: Oct. 15, 2019

(54) DETERMINATION OF PARAMETER VALUES FOR SENSORY SUBSTITUTION DEVICES

(71) Applicant: National ICT Australia Limited, New South Wales (AU)

(72) Inventors: Hendrik Christiaan Stronks, New South Wales (AU); Nick Barnes, New South Wales (AU); Daniel John Parker, New South Wales (AU)

(73) Assignee: National ICT Australia Limited, New South Wales (AU)

( * ) Notice: Subject to any disclaimer, the term of this patent is extended or adjusted under 35 U.S.C. 154(b) by 241 days.

(21) Appl. No.: 15/329,908

(22) PCT Filed: Jul. 28, 2015

(86) PCT No.: PCT/AU2015/050425
§ 371 (c)(1),
(2) Date: Jan. 27, 2017

(87) PCT Pub. No.: WO2016/015099
PCT Pub. Date: Feb. 4, 2016

(65) Prior Publication Data
US 2017/0231865 A1    Aug. 17, 2017

(30) Foreign Application Priority Data

Jul. 28, 2014  (AU) .............................. 2014902915

(51) Int. Cl.
*A61H 23/02* (2006.01)
*G08B 6/00* (2006.01)
*A61F 9/08* (2006.01)

(52) U.S. Cl.
CPC .............. *A61H 23/02* (2013.01); *A61F 9/08* (2013.01); *G08B 6/00* (2013.01)

(58) Field of Classification Search
None
See application file for complete search history.

(56) References Cited

U.S. PATENT DOCUMENTS 6,430,450 B1    8/2002  Bach-Y-Rita et al.
2006/0165311 A1*  7/2006  Watson ................. G06T 7/0002
                                                            382/286

(Continued)

FOREIGN PATENT DOCUMENTS

DE    102008039153 A1    2/2010
EP        1903432 A2     3/2008

(Continued)

OTHER PUBLICATIONS

Ogrinc et al., Sensory Integration of Apparent Motion Speed and Vibration Magnitude, Nov. 15, 2017, IEEE, IEEE Transactions on Haptics, vol. 11, No. 3, pp. 455-463 (Year: 2017).*

(Continued)

*Primary Examiner* — Carlos Garcia
(74) *Attorney, Agent, or Firm* — Kilpatrick Townsend & Stockton LLP

(57) ABSTRACT

The present disclosure provides a computer-implemented method for representing intensity levels indicative of a first type of sense of a subject (150) by parameter values for a different second type of sense of the subject (150). The method comprises determining (210) a first parameter value for the second type of sense representing a first intensity level indicative of the first type of sense; and determining (220) a second parameter value for the second type of sense representing a second intensity level indicative of the first type of sense with reference to the first parameter value, wherein the first parameter value differs from the second parameter value by at least one Just-Noticeable-Difference (JND) of the second type of sense of the subject (150).

20 Claims, 10 Drawing Sheets

(56) References Cited

U.S. PATENT DOCUMENTS

| | | | |
|---|---|---|---|
| 2011/0043537 A1* | 2/2011 | Dellon | G09B 9/00 345/647 |
| 2011/0285667 A1* | 11/2011 | Poupyrev | G06F 3/016 345/174 |
| 2011/0313315 A1* | 12/2011 | Attias | A61B 5/12 600/559 |
| 2012/0327006 A1* | 12/2012 | Israr | G06F 3/016 345/173 |
| 2014/0184384 A1 | 7/2014 | Zhu et al. | |
| 2016/0258758 A1* | 9/2016 | Houston | G01C 21/20 |
| 2017/0259060 A1* | 9/2017 | McCarthy | A61N 1/0531 |

FOREIGN PATENT DOCUMENTS

| | | |
|---|---|---|
| WO | 2010145013 A1 | 12/2010 |
| WO | 2012/104626 A1 | 8/2012 |
| WO | 2012104626 A1 | 8/2012 |
| WO | 2013018090 A1 | 2/2013 |

OTHER PUBLICATIONS

Bermejo et al. A survey on haptic technologies for mobile augmented reality, Sep. 12, 2017, Hong Kong University of Science and Technology, pp. 1-24 (Year: 2017).*

Horvath et al., FingerSight: Fingertip Haptic Sensing of the Visual Environment, Mar. 6, 2014, IEEE Journal of Translational Engineering in Health and Medicine, vol. 2, 2014, 2700109 (Year: 2014).*

International Search Report and Written Opinion of PCT/AU2015/050425 dated Sep. 3, 2015, 10pages.

Mann, S. et al., "Blind Navigation with a Wearable Range Camera and Vibrotactile Helmet", In: Proceedings of the 19th ACM international conference on Multimedia (MM 2011), pp. 1325 to 1328. ACM (2011).

Extended European Search Report of EP 15828148.5 dated Mar. 8, 2018, 9 pages.

* cited by examiner

300

(a) Input Image (b) Rescaled Image (c) Down-sampled Image (d) Tactility Stimulation Levels (in Volts)

(e) Tactility Stimulation Levels (in Volts)

(a) Input Image (b) Tactile Stimulus Levels

DETERMINATION OF PARAMETER VALUES FOR SENSORY SUBSTITUTION DEVICES

CROSS-REFERENCE TO RELATED APPLICATIONS

The present application is a national phase filing of PCT/AU2015/050425 filed on 28 Jul. 2015, which claims priority from the Australian provisional application 2014902915 filed on 28 Jul. 2014 with National ICT Australia being the applicant and the contents of which are incorporated herein by reference.

TECHNICAL FIELD

The present invention generally relates to sensory substitution devices and methods. Aspects of the invention include computer-implemented methods, software, a computer system for determining parameter values for sensory substitution devices, and a sensory substitution device.

BACKGROUND

A sensory substation device translates a type of sensory indication to another type of sensory indication, for example from a visual indication, an auditory indication or a ranging indication to a tactility indication to facilitate perception of the visual, auditory or ranging indication by tactility of a subject.

Particularly, tactile vision substitution devices translate a visual image into an array of voltage signals that drive an array of motors to generate vibrations applied to the subject. The image may be perceived using the vibrations by the subject using the tactile sense. This is particularly relevant to blind people, but can be extended to other areas ranging from heavy industry to defence, by alleviating the informational burden on the visual system of the subject.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

There is provided a computer-implemented method for representing intensity levels indicative of a first type of sense of a subject by parameter values for a different second type of sense of the subject, comprising:
  determining a first parameter value for the second type of sense representing a first intensity level indicative of the first type of sense; and
  determining a second parameter value for the second type of sense representing a second intensity level indicative of the first type of sense with reference to the first parameter value;
  wherein the first parameter value differs from the second parameter value by at least one Just-Noticeable-Difference (JND) of the second type of sense of the subject.

It is an advantage that the invention takes into account the first parameter value for the second type of sense in determining the second parameter value for the second type of sense to represent the second intensity level indicative of the first type of sense. The second parameter value determined according to the invention differs from the first parameter value by at least one JND of the second type of sense, which evokes stimuli for the second type of sense that are distinguishable to the subject. As a result, the invention provides, in the form of the second type of sense, better representation of contrast information in the first type of sense.

Determining the first parameter value for the second type of sense may comprise:
  determining a plurality of parameter values for the second type of sense of the subject that are distinguishable to the subject based on JNDs of the second type of sense; and
  selecting one of the plurality of parameter values for the second type of sense being the first parameter value.

Selecting the one of the plurality of parameter values may comprise:
  determining a value range of the intensity levels indicative of the first type of sense;
  dividing the value range into a plurality of intervals based on JNDs of the first type of sense of the subject, wherein the number of the plurality of intervals is equal to the number of the plurality of parameter values for the second type of sense; and
  selecting, based on the plurality of intervals, the one of the plurality of parameter values for the second type of sense being the first parameter value.

The plurality of parameter values for the second type of sense may comprise all parameter values for the second type of sense that are distinguishable to the subject.

Using all available parameter values may ensure that the contrast information of the first type of sense is preserved in the second type of sense as much as possible.

Determining the second parameter value for the second type of sense may further comprise:
  selecting another one of the plurality of parameter values for the second type of sense being the second parameter value.

The first type of sense may comprise visual perception, auditory perception, ranging perception, gustatory perception, olfactory perception, vestibular perception.

The second type of sense may comprise tactility and the parameter values for the second type of sense may comprise electric voltage and electric current.

The first intensity level indicative of the first type of sense may comprise a first visual intensity level indicative of a first portion of an image including a plurality of portions.

The second intensity level indicative of the first type of sense may comprise a second visual intensity level indicative of a second portion of the image.

The second portion of the image may comprise at least part of a Region of Interest (ROI) of the image.

The ROI may comprise a region in which the intensity levels change over time.

The ROI may comprise a moving object in the image.

The ROI may comprise an edge in the image.

The ROI may comprise a scene object in the image.

The above computer-implemented method may further comprise adjusting the parameter values for the second type of sense over time to counter adaptation to the second type of sense.

The above computer-implemented method may be performed by a sensory substitution system, and the second parameter value is provided as input to a sensory output device.

The first intensity level may differ from the second intensity level less than one Just-Noticeable-Difference (JND) of the first type of sense of the subject.

There is provided a computer software program, including machine-readable instructions, when executed by a processor, causes the processor to perform the method of any one of the preceding claims.

There is provided a computer system for representing intensity levels indicative of a first type of sense of a subject by parameter values for a different second type of sense of the subject, the computer system comprising:
- a memory to store instructions;
- a bus to communicate the instructions from the memory;
- a processor to perform the instructions from the memory communicated via the bus:
  - to determine a first parameter value for the second type of sense representing a first intensity level indicative of the first type of sense; and
  - to determine a second parameter value for the second type of sense representing a second intensity level indicative of the first type of sense with reference to the first parameter value;
  - wherein the first parameter value differs from the second parameter value by at least one Just-Noticeable-Difference (JND) of the second type of sense of the subject.

There is provided a sensory substitution system for translating intensity levels indicative of visual information to intensity levels indicative of tactile perception of a subject, comprising:
- a sensory information capture device to capture the intensity levels indicative of visual information;
- an array of stimulation generation members; and
- a processor
  - to determine a first parameter value for tactile perception representing a first intensity level indicative of visual information; and
  - to determine a second parameter value for tactile perception representing a second intensity level indicative of visual information with reference to the first parameter value;
  - wherein the first parameter value differs from the second parameter value by at least one Just-Noticeable-Difference (JND) of tactile perception of the subject.

The sensory information capture device may comprise a camera.

The stimulation generation device may comprise a coin motor or an electrode.

BRIEF DESCRIPTION OF THE DRAWINGS

Features of the present disclosure are illustrated by way of non-limiting examples, and like numerals indicate like elements, in which.

BEST MODES OF THE INVENTION

Figure 1:
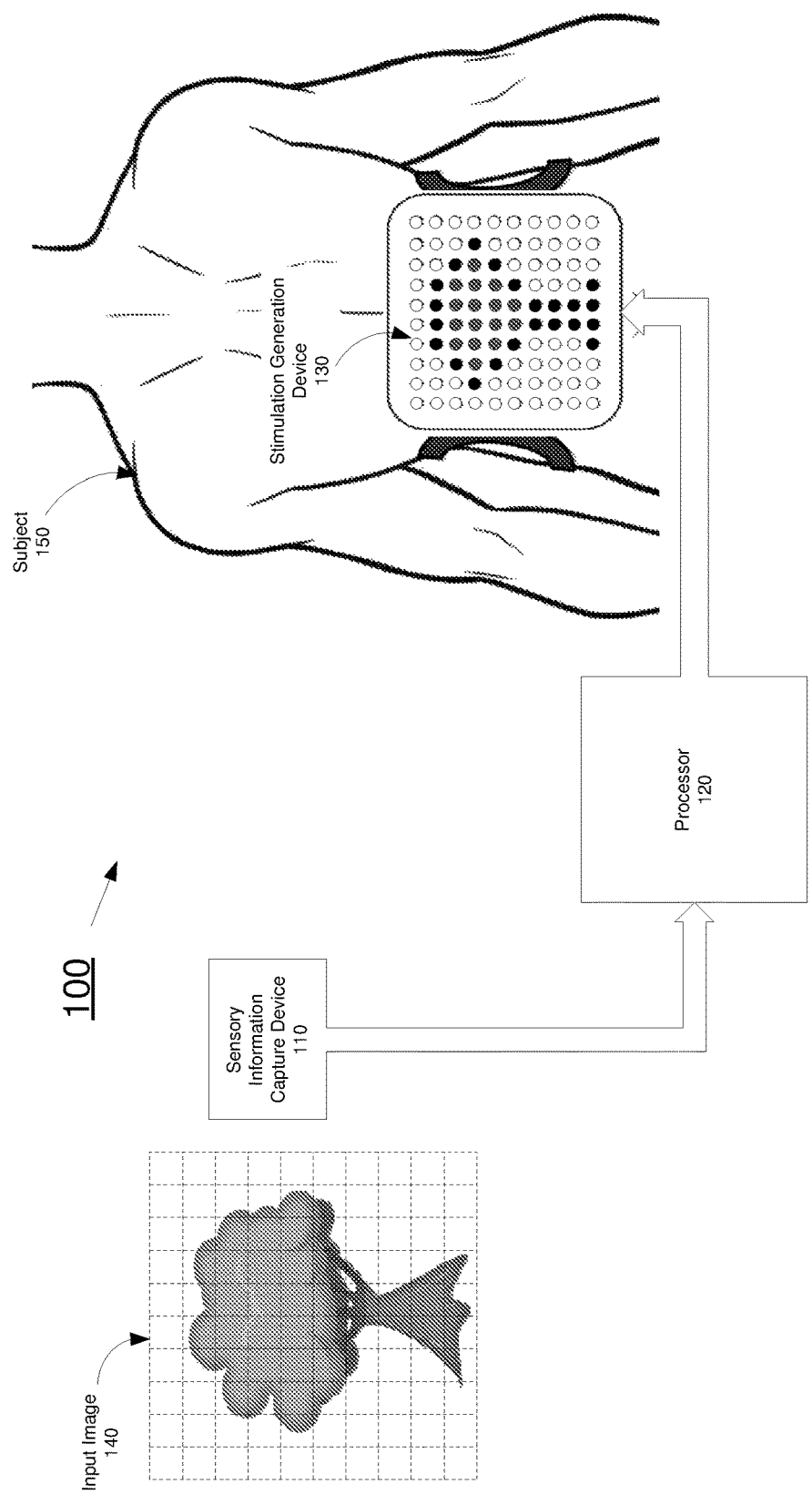
FIG. 1 is a diagram of a sensory substitution device for translating a first type of sense to a different second type of sense according to an example of the present disclosure.

FIG. 1 is a diagram of a sensory substitution system 100 for translating a first type of sense to a different second type of sense. The sensory substation system 100 includes a sensory information capture device 110, a processor 120 and a sensory output device, such as an array of stimulation generation devices 130.

The sensory information capture device 110 is used to detect (capture) sensory information representing the first type of sense of a subject 150 for example a person. The sensory information does not have to be what the person actually perceives especially when the perception capability of the person in the first type of sense is impaired, for example, a blind person who cannot perceive meaningful visual information. The sensory information captured by the sensory information capture device 110 provides a meaningful representation of what the person perceives in a normal case or what the person would perceive if the perception capability of the person is not impaired.

In the example shown FIG. 1, although the sensory information capture device 110 is shown as a camera capturing visual information, particularly image 140, representing visual sense of the subject 150, the sensory information capture device 110 may be one or more of a variety of sensory information capture devices to capture sensory information representing other sense types, for example auditory perception or sound, ranging perception or distance, gustatory perception or taste, olfactory perception or smell, vestibular perception or balance, or any other perceptions.

The sensory information capture device 110 communicates data including colour, sound, depth, etc. representing intensity levels indicative of the first type of sense to the processor 120. That is, the intensity levels indicate the actual measurable amounts of the sense across a range of suitable intensity levels for that sense. The intensity levels can be the actual measurable amounts of the sense or take other forms from which the actual measurable amounts of the sense can be derived.

In the example shown in FIG. 1, a single intensity level may be represented by a colour value of a pixel of the image 140. In the case of a black-and-white image, the intensity level may be represented by an intensity (grey level) of the pixel of the image 140 when compared to a grey range or grey scale.

Ideally, each pixel of the image 140 correspond to one stimulation generation device 130, however it is usually impractical to have a large number of stimulation generation devices 130 placed on the subject 150. For example, if the image 140 is an image of 100×100 pixels, the array of stimulation generation members 130 needs to include 10,000 stimulation generation members to have one to one relationship to the image 140, which is usually too expensive and may cause physical burden to the subject 150. Therefore, the image 140 may be partitioned into a plurality of portions, shown as the dash grid in FIG. 1, which may be referred to as input channels thereinafter.

In this example, the dash grid includes 10×10 input channels with each of them corresponding to one stimulation generation device 130. The intensity level of each input channel may be represented by an averaged or weighted sum of the grey level (intensity) of the pixels in the portion. In other examples, the intensity level of an input channel may include a consideration of neighbouring input channels or pixels.

The intensity levels of the input channels are processed by the processor 120 to be represented by parameter values for the second type of sense of the subject 150.

Specifically, the processor 120 translates the intensity levels indicative of the first type of sense to the parameter values for the second type of sense. Based on the parameter values, the processor 120 drives the array of stimulation generation members 130 to generate stimuli to the subject 150 in the form of the second type of sense. The stimulation generation members 130 may be referred to as output channels hereinafter.

Similarly to the first type of sense, the second type of sense may include a variety of senses. For ease of description, the second type of sense in this example is tactility of the subject 150.

In this example, the tactile stimuli may take the form of vibrations produced by the array of stimulation generation members 130 for example motors 130, particularly coin motors. The parameter values for tactility may be electrical voltages applied to the array of motors 130. Alternatively, the actual electrical voltages may be based on the parameter values.

As shown in FIG. 1, the array of motors 130 is also an array of 10×10 motors, which are placed on the lower back of subject 150 in a rectangular arrangement. The rectangular arrangement of the array of motors 130 allows each motor 130 to spatially correspond to the arrangement of an input channel of the image 140. It should be noted that, in other examples, the position and arrangement of the array of motor 130 may be different from the example shown in FIG. 1 without departing from the scope of the invention. For example, the array of motors can be located on the chest of the subject 150 or be circular in shape.

The intensity level of each input channel of the image 140 are translated to a voltage value for the corresponding motor 130 or output channel, which the processor 120 applies to the motor 130 in order to cause the motor 130 to generate a tactile stimulus to the subject 150.

As a result, the array of motors 130 generate a tactile stimulus pattern on the lower back of the subject 150, represented by the round dots in FIG. 1. For description purposes here, the grey levels of the round dots represent vibration strength levels at different locations on the lower back of the subject 150, which may be perceived by the subject 150 as the image 140.

In other examples, the tactile stimuli may be generated, in the form of electrical current, by an array of electrodes 130 placed on the tongue of the subject 150, not shown in FIG. 1.

Figure 2:
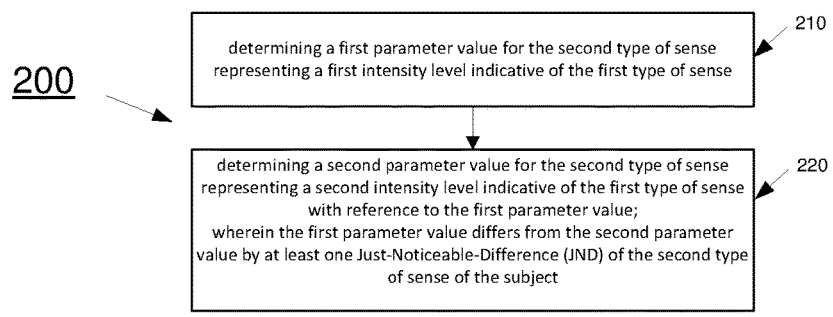
FIG. 2 is a flow chart for representing intensity levels indicative of a first type of sense of a subject by parameter values for a different second type of sense of the subject according to an example of the present disclosure.
Figure 3:
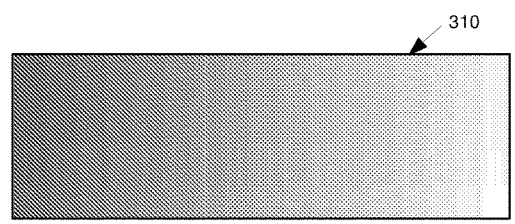
FIGS. 3a to 3e shows a process for processing an input image to determine voltage values for an array of motors according to an example of the present disclosure.
Figure 3:
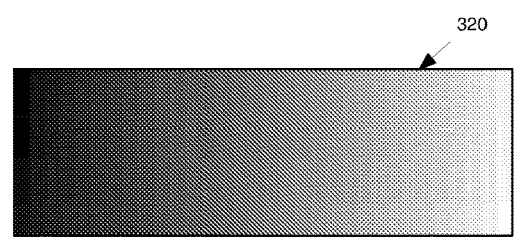
Figure 3:
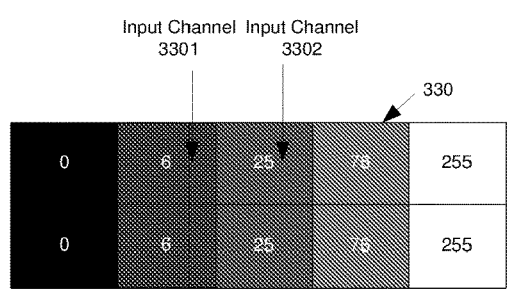
Figure 3:
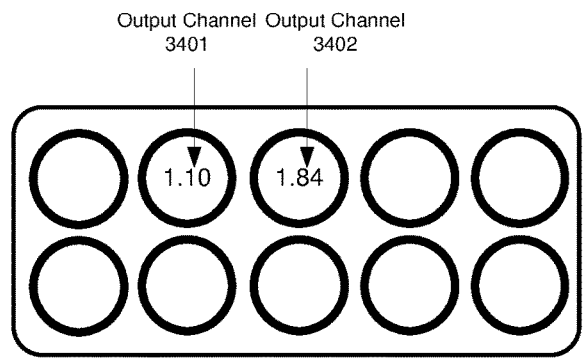
Figure 3:
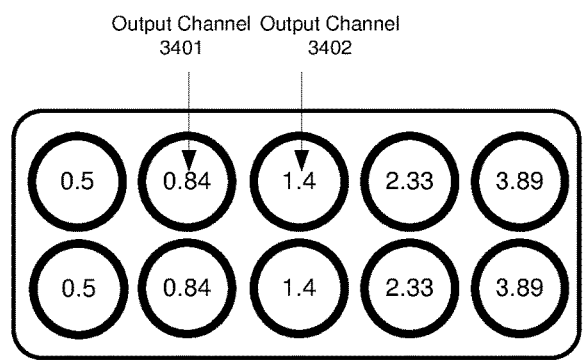

FIG. 2 shows a process 200 for representing intensity levels indicative of a first type of sense of a subject by parameter values for a different second type of sense of the subject.

The process 200 shown in FIG. 2 may be performed by the processor 120 in this example. In other examples, the process 200 may be performed by a separate and optionally remote computing device, for example, a computer system shown in FIG. 9.

A detailed example of operation of the sensory substitution system 100 shown in FIG. 1 will now be described with reference to FIGS. 2 to 8*d*.

An image is captured by the sensory information capture device 110 as an input image 310. The sensory information capture device 110 may be a black-and-white camera or a colour camera. As a result, the input image 310 may be a black-and-white or colour input image. For ease of description, the input image 310 in this example is a grey level image as shown in FIG. 3*a*, which may be captured by a black-and-white camera or translated from a colour image captured by a colour camera. In other examples, a colour input image may be used.

The input image 310 is sent to the processor 120 for further processing.

The dynamic range of grey levels in the input image 310, although not always, may contain a relatively small range of grey levels, for example, from light grey to white, as shown in FIG. 3*a*. The range is of grey levels (intensities) in the input image 310 is dynamic as it depends on the content of the input image. As a result, the input image 310 may contain limited contrast information, which makes it difficult to preserve the contrast information in the form of tactile stimuli generated by the array of motors 130.

To mitigate this effect, the input image 310 is rescaled to contain a larger range of grey levels, for example, from black to white, as shown in FIG. 3*b*, which results in a rescaled image 320.

As described before, it is usually not practical to have as many motors as the number of pixels in the rescaled image 320 in the sensory substitution system 100. Therefore, the number of pixels in the rescaled image 320 may be down-sampled.

The down-sampling of the pixels in the rescaled image 320 may include two aspects: determining the number of input channels and determining the grey levels of the input channels.

In this example, the rescaled image 320 is down-sampled to have the same number of input channels as the number of output channels, which means both the array of input channels and the array of output channels include 2×5 channels.

The grey level of each input channel may be determined on a certain scale. This can be done by varying methods such as averaging the grey levels of all pixels over the input channel, or putting more weight on the edge of the input channels to enhance edge detection, or more weight on the centre, etc. The down-sampled image 330 is shown in FIG. 3*c*, which includes 2×5 input channels. The number in each input channel in FIG. 3*c* indicates the grey level of the input channel.

It should be noted that although in this example rescaling the image is performed prior to down-sampling the image, the order the two steps may be switched in other examples without departing from the scope of the invention. Further, one or both of the steps may be omitted.

The grey level range of all the input channels in the down-sampled image 330 may be determined on a certain scale (scales can be logarithmic or linear or any other scale). For example, the grey level range of the down-sampled image 330 is 0 to 255 in linear scale.

In this example, a (previous) voltage value (referred to as a first parameter value) translated from a (previous) grey level (referred to as a first intensity level) serves as a reference parameter value for translating a subsequent grey level (referred to as a second intensity level) to a subsequent parameter value (referred to as a second parameter value). The first parameter value and the second parameter value may cause a first tactile stimulus and a second tactile stimulus that are distinguishable to the subject 150.

In other words, the perception by the subject 150 of the second tactile stimulus differs from that of the first tactile stimulus by at least one Just-Noticeable-Difference (JND), which is the minimal difference that can be perceived by the subject 150.

Generally speaking, JND is a term related to distinguishing perceptions by a subject of stimulus levels at a correct rate, however, for ease of description, in the present specification, the minimal difference between two voltage values that cause perceptions of tactile stimuli at the correct rate that are one JND apart is also referred to as a JND. For example, if the perception of a tactile stimulus caused by a voltage value of 2.0 volts is one JND apart from the perception of a tactile stimulus caused by a voltage value of 2.3 volts at a correct rate of 85%, the JND represented in volts at the correct rate of 85% is 0.3 volts.

It should be noted that a specific JND may be used with reference to a reference parameter value. For example, further to the above example, the JND of 0.3 volts is only valid with reference to the voltage value of 2.0 volts. The next voltage value that may cause a minimal distinguishable tactile stimulus with reference to 2.3 volts may not simply be 2.3+0.3=2.6 volts. However, previous study indicates that the ratio of the JND and the corresponding reference parameter value is a constant, i.e., $$k = \frac{JND}{ref},$$

which is called Weber's fraction.

In the above example, Weber's fraction is 0.3/2.0=0.15. With Weber's fraction, it can be determined that the next voltage value one JND apart with reference to 2.3 volts is $2.3+JND_{ref=2.3}=2.3+2.3\times k=2.3\times(1+k)=2.645$ volts, which means that the parameter value of 2.645 volts may evoke a minimal distinguishable tactile stimulus with reference to 2.3 volts at the correct rate of 85%.

The subsequent voltage values, e.g., 3.042 volts, 3.498 volts, 4.023 volts, 4.626 volts, may be determined in a similar way subject to the maximal voltage value that can be applied to the motors 130 or the subject 150 is comfortable with, for example, 5.0 volts in the above example.

On the other hand, the first voltage value below the voltage value of 2.0 volts that is one JND apart is 2.0/(1+k)=1.739 volts. The subsequent voltage values, e.g., 1.512 volts, 1.315 volts, 1.144 volts, can be determined in a similar way subject to the minimal voltage value or perception threshold that can cause a perceivable tactile stimulus to the subject 150, for example 1.0 volt in the above example. In other words, any voltage values below the perception threshold may not cause perceivable tactile stimuli to the subject 150.

The number of the JNDs is determined by the following equation:

$$\#JNDs = \frac{\text{dynamic range}}{\text{JND fraction}} = \frac{\log(MCL/\text{perception threshold})}{\log((JND+I)/I)} \quad (1)$$

wherein #JNDs=number of available JNDs, MCL=$^{10}$log (maximal comfortable stimulus level) in % duty cycle (dc), and I=$^{10}$log(reference stimulus level) in % dc.

The maximal comfortable stimulus level and perception threshold for each motor 130 with regard to the subject 150 may be determined by increasing the stimulus level from 0 to 100% duty cycle (% dc) in steps of 10% in an initial testing phase. In the above example, 100% dc corresponds to 5V.

Based on the JNDs or the number of JNDs, the number of voltage values that are one JND apart within the range defined by the perception threshold and the maximal comfortable stimulus level may be determined. Clearly, the number of voltage values as described in the above example is 11.

Now referring back to FIG. 3, it should be noted that the first intensity level and the second intensity level may represent the intensity levels of the same input channel at different moments or the intensity levels of different input channels at the same moment. In this example, the first intensity level is represented by the grey level (6) of the input channel 3301, while the second intensity level is represented by the grey level (25) of the input channel 3302. The output channels that are spatially correspond to the input channels 3301 and 3302 are output channels 3401 and 3402, respectively.

Figure 4:
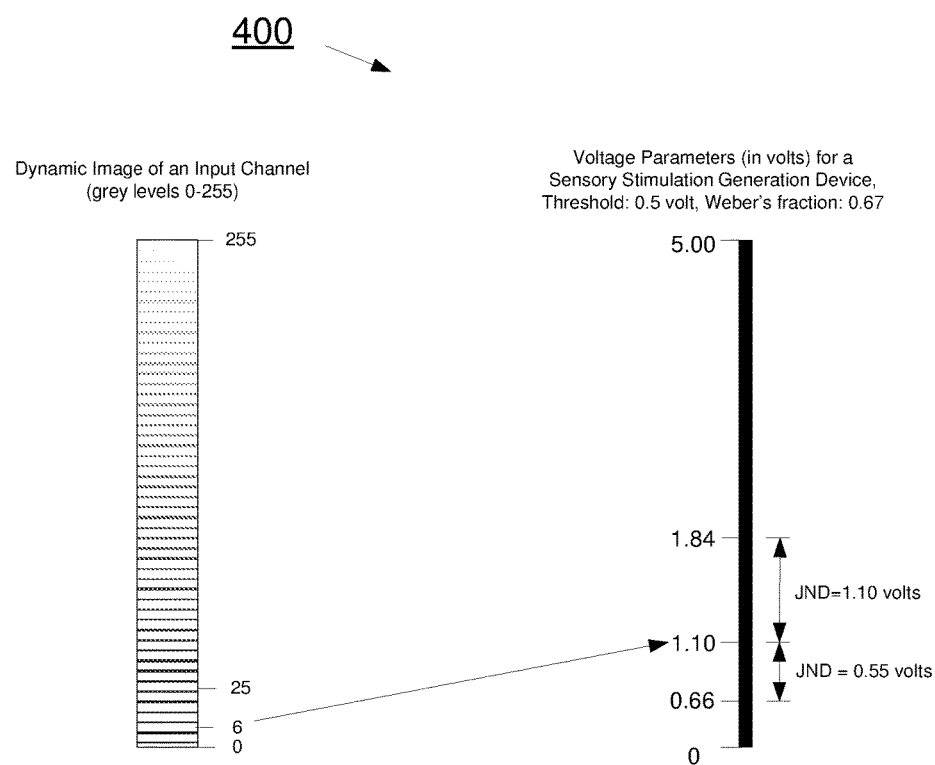
FIG. 4 illustrates an example of determining a subsequent voltage value with reference to a previous voltage value according to an example of the present disclosure.
Figure 5A:
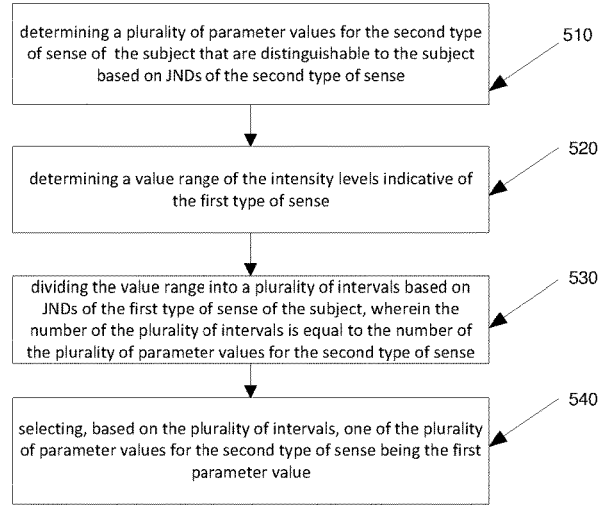
FIGS. 5a and 5b illustrate an example for mapping an intensity level indicative of the first type of sense to a parameter value for the second type of sense.
Figure 5B:
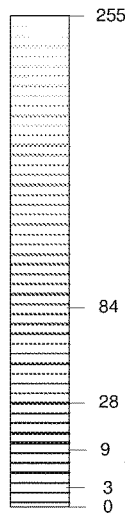
Figure 5B:
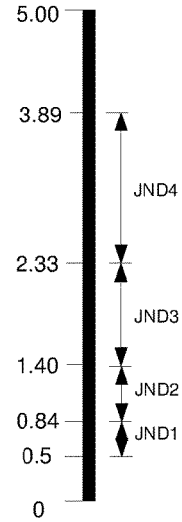
Figure 6:
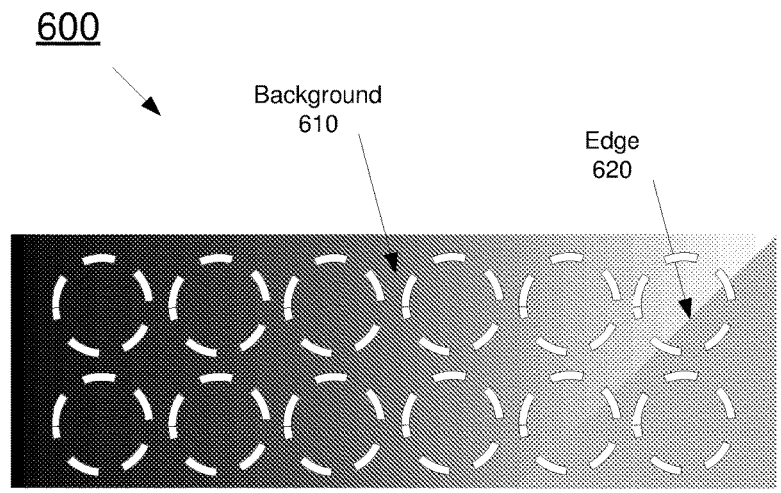
FIGS. 6a and 6b illustrate a scenario where an example of the present disclosure is applied to an image containing an edge.
Figure 6:
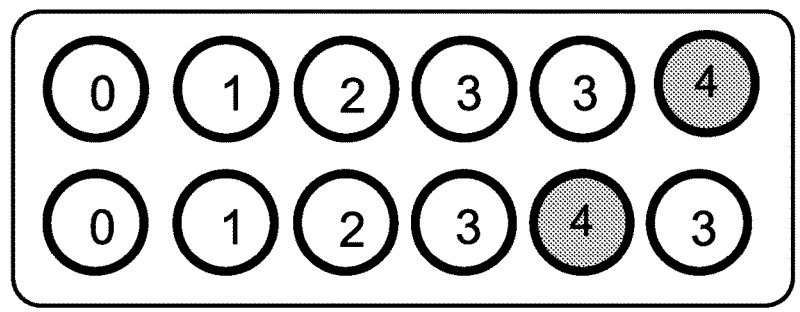
Figure 7:
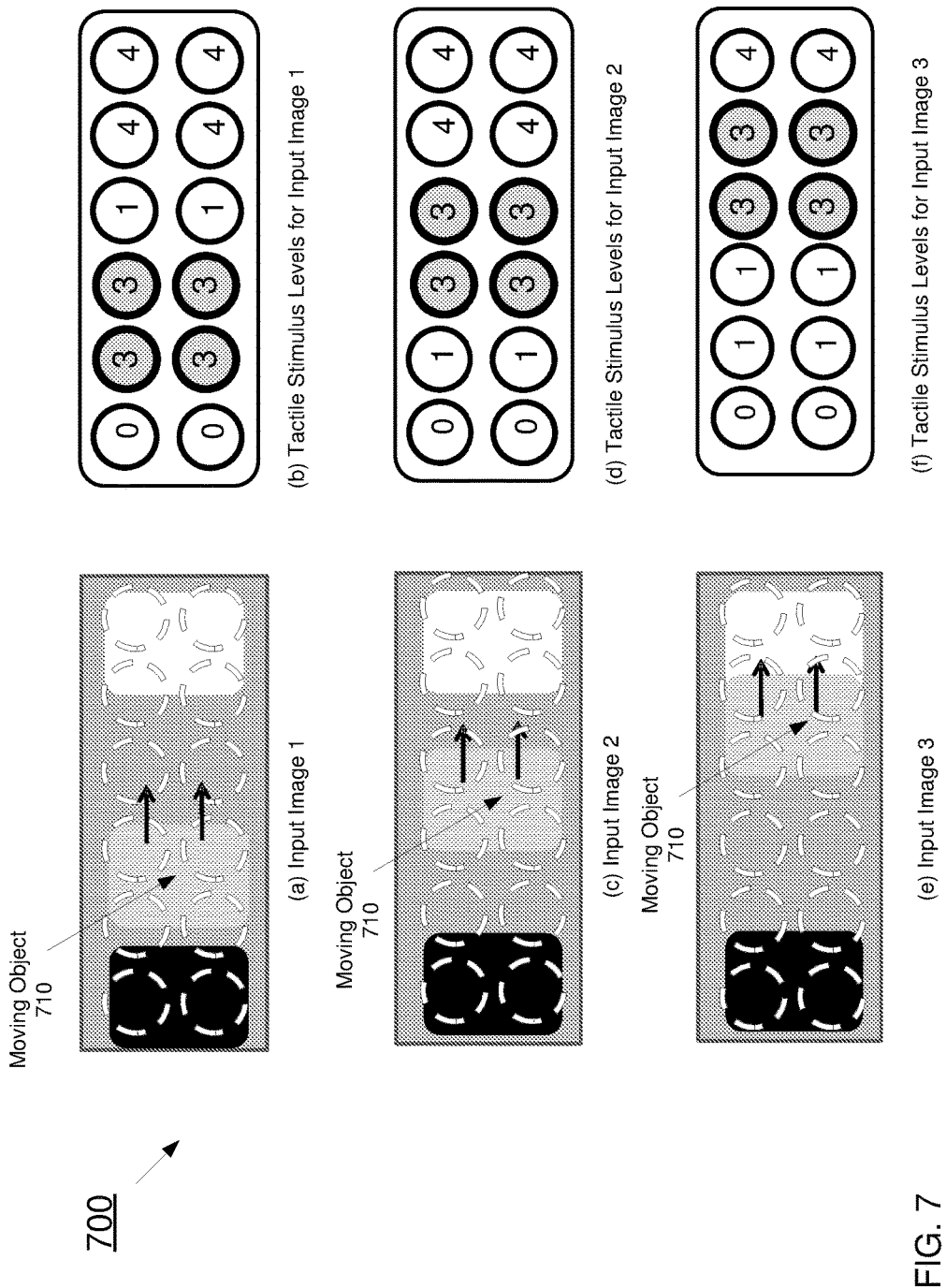
FIGS. 7a to 7f illustrate a scenario where an example of the present disclosure is applied to an image containing a moving object.
Figure 8:
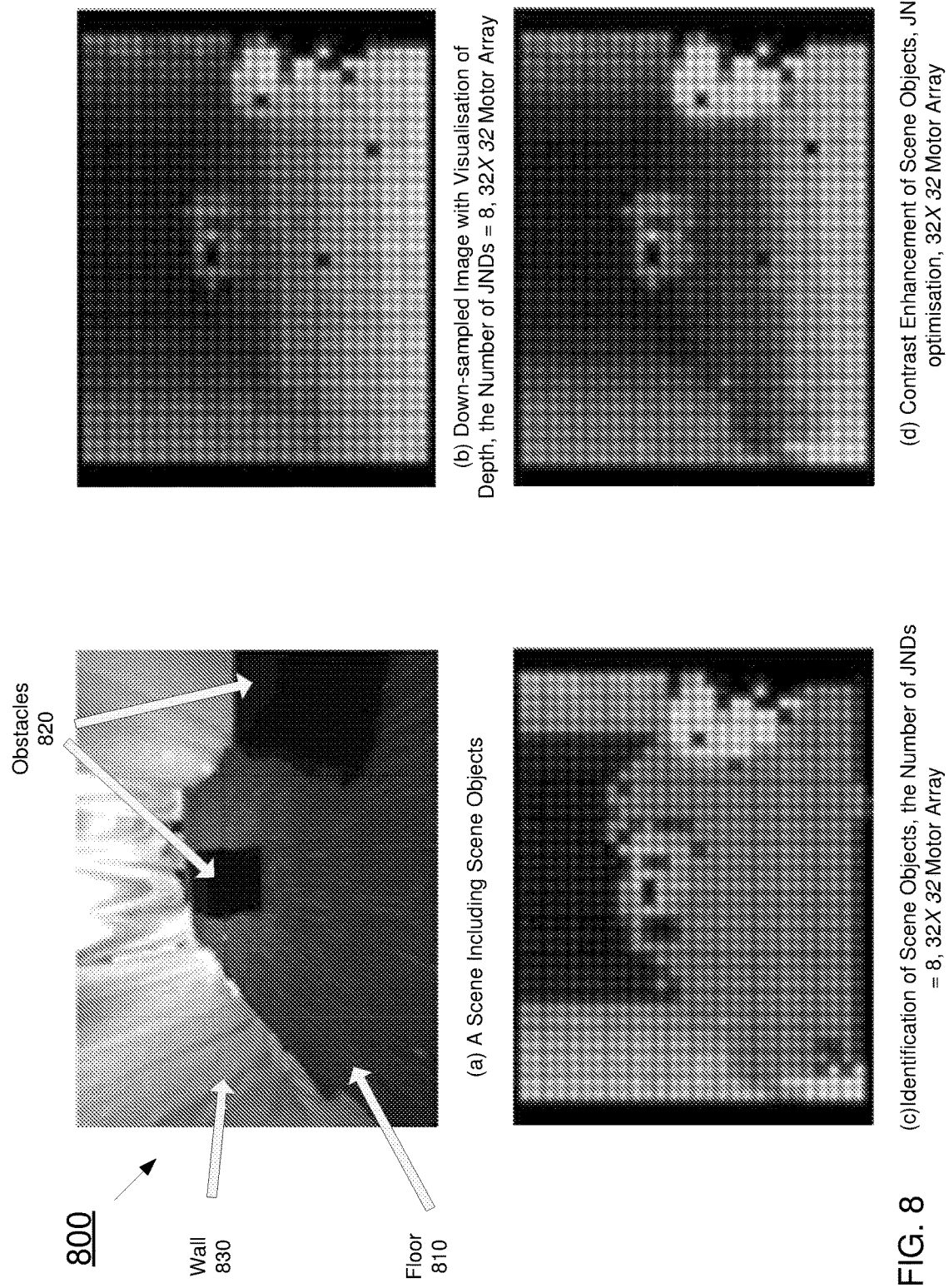
FIGS. 8a to 8d illustrate a scenario where an example of the present disclosure is applied to an image containing scene objects.

In the examples shown in FIGS. 4 and 5b, the perception threshold is 0.5 volts, the maximal voltage value is 5.0 volts, and Weber's fraction is 0.67.

The processor 120 determines 210 a voltage value of 1.1 volts for the output channel 3401, as shown in FIG. 3d, to represent the grey level (6) of the input channel 3301.

The processor 120 then determines 220, based on the Weber's fraction and the reference voltage value of 1.1 volts, one or more voltage values for the output channel 3402 that are at least one JND apart from the reference voltage value, which may be for example 0.66 volts, 1.84 volts, as shown in FIG. 4. That is, the one or more voltage values for the output channel 3402 is determined with reference to, particularly, relative to, the reference voltage value.

Therefore, the processor 120 may use any voltage values above 1.84 volts or below 0.66 volts for the output channel 3402 to represent the grey level (25) of the input channel above subject to the maximal voltage value of 5.0 volts and the perception threshold of 0.5 volts for the output channel 3402, as shown in FIG. 3d.

This is particularly useful when the grey levels of the input channels are close. For example, the difference between the grey levels of input channels may be less than one JND of the first type of sense of the subject. As a result, no matter how close the grey levels of the input channels are, the voltage values for the corresponding output channels are forced to differ by at least one JND of the second type of sense of the subject, which may cause different tactile stimuli that can be perceived by tactility of the subject 150. Therefore, the perceivable difference in tactile stimuli is guaranteed. This provides a better perception of a particular portion in the image 330 for example a Region of Interest (ROI).

FIGS. 5a and 5b illustrate an example of determining the voltage value for the output channel 3401 being the first parameter value. It should be noted that the voltage value for the output channel 3401 may be determined in different ways without departing from the scope of the invention.

As the maximal voltage value, the perception threshold and Weber's fraction for the output channels are known factors for example upon initialisation with respect to the subject 150, the processor 120 may determine 510 a plurality of voltage values for the output channels that are distinguishable to the subject 150 based on JNDs of the output channels starting from for example the perception threshold.

As shown in FIG. 5b, the plurality of voltage values starting from the perception threshold may be 0.5 volts, 0.84 volts, 1.40 volts, 2.33 volts and 3.89 volts. In this example, all the five available voltage values starting from the perception threshold are taken into account to preserve as much contrast information of the input channels as possible in the output channels. In other examples only some of them may be used without departing from the scope of the invention. The processor 120 selects one of the plurality of voltage values for the output channel 3401 being the first parameter value. The selecting of the one of the plurality of voltage values is described in detail below.

The processor 120 determines 520 a value range or dynamic range of the grey levels of the input channels. As shown in FIGS. 3c and 5b, the dynamic range of the input channels is 0 to 255 in linear scale.

The processor 120 divides 530 the dynamic range of the input channels into a plurality of intervals, wherein the number of the plurality of intervals is equal to the number of the plurality of voltage values for the output channels, which is five in this example.

It should be noted although the dynamic range of the grey levels of input channels can divided in different ways, the division of the grey levels shown in FIG. 5b is based on JNDs of visual perception of the subject 150 according to equation (1) described above to preserve distinguishable visual perception in the division. It should be noted that if the subject 150 is a blind person, the JNDs of visual perception used to divide the grey levels may be determined based on empirical or statistical results. This way the contrast information of the image that can be perceived by visual perception may be preserved as much as possible in the output channels and still be perceived by tactile perception.

As shown in FIG. 5b, the dynamic range of the input channels are divided into 5 intervals, 0 to 3, 3 to 9, 9 to 28, 28 to 84 and 84 to 255.

The translating of the grey levels to the voltage values may be performed based on a mapping table as below.

| Grey levels of input channels | Voltage values of output channels |
| --- | --- |
| 0 to 3 | 0.50 |
| 3 to 9 | 0.84 |
| 9 to 28 | 1.40 |
| 28 to 84 | 2.33 |
| 84 to 255 | 3.89 |

The processor 120 may select 540, based on the intervals in the above mapping table, one of the plurality of voltage values as the voltage value for the output channel corresponding to the input channel by mapping the grey level intervals to the voltage values. For example, the grey level of the input channel 3301 is 6 as shown in FIG. 3c, which falls into the interval of 3 to 9, the processor 120 maps the grey level of the input channel 3301 to the voltage value of 0.84 volts for the corresponding output channel 3401.

The above process, referred to as JND-optimised mapping, may be used to translate grey levels of input channels representing a particular portion of the input image for example the background or the entire input image, to voltage values for corresponding output channels.

For the neighbouring input channel 3302, the grey level of which is 25, the processor 120 may determine another voltage value in the plurality of voltage values other than 0.84 volts for the corresponding output channel 3402, which is at least one JND apart from the voltage value for the output channel 3401, for example, 1.4 volts, as shown in FIG. 3e.

The above method may be applied to many scenarios, which will be described below.

JND-Optimised Mapping

FIG. 3e illustrates a scenario where the above described JND-optimised mapping is applied to the entire image 330 according to the scales shown in FIG. 5b. It can be seen from FIG. 3e that the voltage values for output channels are at least one JND apart. As a result, the subject 150 may perceive, via tactile perception, spatial changes to the grey levels of the image 330.

Spatiotemporal Contrast Enhancement

If the grey levels of one or more input channels as determined in the image 330 change from one frame (a frame is an image or collection of input pixels) to the next, these channels may be referred to as channel of interest (COI). The COIs may be adjacent or at least close to each other forming a region-of-interest (ROI). In this case, contrast enhancement is prioritised for the ROI by assigning at least one more or less JND compared to the surrounding, temporally unchanging or less changing output channels, even if the grey level of a ROI input channel and that of a non-ROI input channel in a spatial sense fall into the same grey level interval shown in FIG. 5b. As a result, the changing output channels and the unchanging or less changing output channels may be distinguishable to the subject 150.

ROIs may be detected in a plurality of ways based on spatiotemporal contrast characteristics of input channels. ROIs may also be detected based on the output channel characteristics.

The ROI may be detected by a region detector, an edge detector, or their combination. A person skilled in the art may also take various other features into account such as motion, texture, distance (in a depth image for example). One may also use machine learning approaches to develop a region detector from a set of image examples.

If the difference in grey levels between frames is higher than for example a grey level interval shown in FIG. 5b, the difference in output channel stimulus intensity is at least one JND. Such temporal changes may be detected in a plurality of ways. Temporal resolution is thus accomplished by keeping track of the changes in grey levels of input channels and comparing them with the following frame.

At high frame rates, the average grey level of input channels across successive frames, or some filters, for example a Kalman filter, may be used to prevent artificial grey level changes. For each frame, the voltage values for the output channels may be determined as described with reference to 210 of FIG. 2, particularly, 510 to 540 of FIG. 5a. Spatial contrast of interest may be detected in the input channels and reflected into the ROI output channels, as described with reference to FIGS. 4 and 5b.

Although the above examples are described with reference to a grey level image, a colour image may also be used. Specifically, each colour channel in the colour image is processed as described above and applied to separate motors representing the colour channel. Further, one may take various colour transformations and apply similar approaches.

Edge and Moving Object Contrast Enhancement

Moving objects in the input images may be prioritised over static ones. Further, edges (areas of high contrast) in the input images may be prioritised over areas with less contrast.

For this purpose, standard motion detectors or edge detectors or any other detector (heat/infrared detection, range, UV, stereo camera input, dual camera input, structured light, hyperspectral image data, and ultrasound etc.) may be used to identify one or more ROIs being the moving objects or edges in the input image. As a result, these ROIs may be assigned priority, which results in at least one output channel being assigned to represent these ROIs.

Output channels representing ROIs may be assigned at least one or more JNDs compared to surrounding output channels, as described above. The motion or edge detector may detect the moving objects or edges even if the grey levels of a ROI input channel and that of a non-ROI channel fall into the same grey level interval shown in FIG. 5b.

Upon detection of the moving objects or edges, the motion or edge detector identifies the ROI and non-ROI input channels. The processor 120 assigns at least one more JNDs to the ROI output channels. If the brightness of surrounding non-ROI input channels reaches the maximal grey level, the processor lowers the voltage values for corresponding non-ROI output channels to be one or more JNDs below voltage values for the ROI output channels.

An edge will be represented by assuring at least 1 JND difference of the edge with surrounding output channels. A moving object will be represented as a whole with at least one more JND compared to surrounding output channels or its edge will be presented with enhanced contrast.

FIGS. 6a to 7f illustrate an application of the above described method to an input image containing an edge or a moving object. It should be noted that the circles represented by dash lines in FIGS. 6a to 7f are not part of input images, which are used to represent spatially corresponding output channels. It should also be noted that the numbers in the output channels do not represent the actual voltage values for the output channels, but are used to indicate distinguishable tactile stimulus levels for ease of description. In other words, the tactile stimulus levels are at least one JND apart.

The input image shown in FIG. 6a includes a background portion 610 and an edge 620. As shown in FIG. 6a, the grey level of the background portion 610 changes gradually, while the grey level of the edge 620 changes abruptly compared to surrounding background.

With the JND-optimised mapping applied to the background portion 610, contrast information of the background portion 610 is preserved in corresponding output channels, represented by tactile stimulus levels 0 to 3, as shown in FIG. 6b.

On the other hand, the edge 620 in the input image shown in FIG. 6a is detected by an edge detector. The tactile stimulus level (indicated as "4", as shown in FIG. 6b) caused by the output channels corresponding to the edge 620 are one JND higher than surrounding output channels. As a result, the subject 150 may perceive the contrast information of the background portion 610, and at the same time, have a better perception of the ROI being the edge 620.

FIGS. 7a, 7c and 7e represent a series of images including three frames containing a moving object 710 that may be detected by a motion detector.

By applying the JND-optimised mapping to background and object contrast enhancement to the moving object 710, it can be seen from FIGS. 7b, 7d and 7f that the tactile stimulus level representing the moving object 710 is at least one JND apart from the surrounding regions. This way the subject 150 may perceive that the moving object 710 is "moving" on his or her back without being distracted by background tactile stimuli, which the subject 150 may also perceive.

Importantly, as can be seen from FIGS. 7a to 7f, even if the moving object 710 does not have high contrast relative to the surrounding area, the tactile stimulus levels caused by corresponding output channels are still at least one JND apart from surrounding output channels.

Scene Understanding Enhancement

FIGS. 8a to 8d illustrates a scenario where scene object detectors are used to parse a scene, identifying scene objects in the scene. For ease of description, the tactile stimulus levels of an array of 32×32 output channels are represented by grey levels in this example.

FIG. 8a shows a scene image 800 that includes scene objects or ROIs being a floor 810, obstacles 820 and a wall 830.

FIG. 8b shows the tactile stimulus levels of the output channels translated by conventional methods from the scene image 800. It can be seen from FIG. 8b that the boundaries of the scene objects 810, 820, 830 are not clear.

With the scene object detectors applied to the scene image 800 shown in FIG. 8a, the scene objects 810, 820, 830 are identified, as shown in FIG. 8c.

With the JND-optimised mapping applied to scene image 8(a) with reference to the scene objects identified in FIG. 8c, the tactile stimulus levels of the output channels corresponding to the scene objects 810, 820, 830 is at least one JND apart from surrounding output channels, as shown in FIG. 8d, which makes the boundaries of the scene objects 810, 820, 830 clear while keeping the depth information of the floor object 810.

Fading

Fading is a phenomenon of decreased perceived stimulus intensity during prolonged and constant stimulation, which is a specific form of adaptation. The adaptation to tactile stimuli can be characterized when initialising the sensory substitution system 100 with respect to the subject 150, alongside the perception threshold, JND, the number of JNDs. The perception threshold may be dynamically updated over time. As a result, the dynamic range, the JNDs, the number of JNDs of tactile stimulation, and the voltage values applied to the motors may be updated over time accordingly so as to avoid generation of prolonged and constant tactile stimuli to counter the adaptation to the tactile stimuli.

The above examples can be implemented by hardware, software or firmware or a combination thereof.

Figure 9:
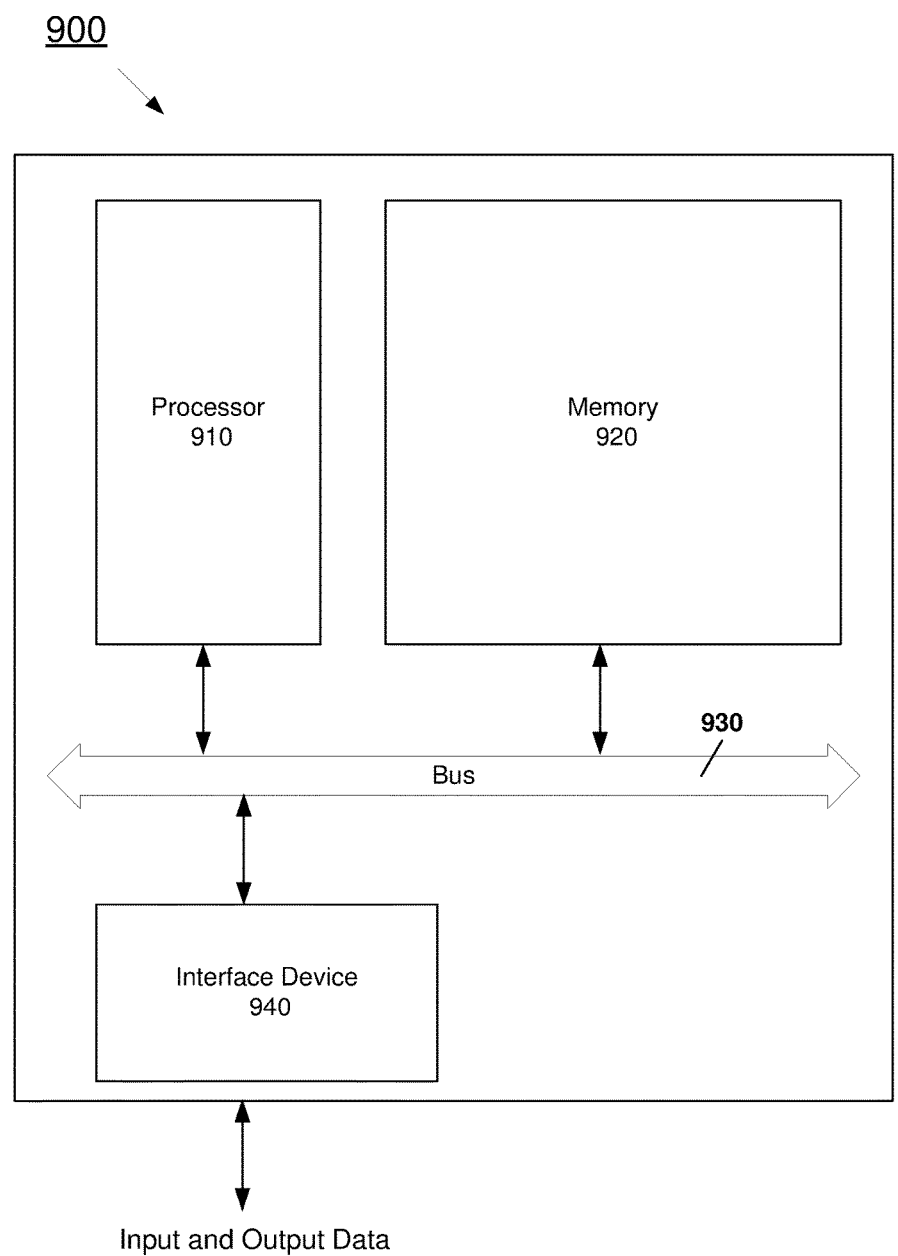
FIG. 9 is a diagram illustrating a computer system for translating a first type of sense to a different second type of sense according to an example of the present disclosure.

FIG. 9 is a diagram illustrating a computer system 900 for representing intensity levels indicative of a first type of sense of a subject by parameter values for a different second type of sense of the subject.

The computer system 900 includes a processor 910, a memory 920, a bus 930 and an interface device 940. The processor 910, the memory 920 and the interface device 940 communicate with each other via the bus 930.

The interface device 940 interfaces with other devices for example a camera to receive data representing a first type of sense for example an image. The data may be communicated to the memory 920 via the bus 930.

The memory 920 stores the data representing the first type of sense and instructions for the processing the data, as described with reference to FIGS. 1 to 8*d*.

The processor 910 may perform the instructions from the memory 620 to determine a first parameter value for the second type of sense representing a first intensity level indicative of the first type of sense; and determine a second parameter value for the second type of sense representing a second intensity level indicative of the first type of sense with reference to the first parameter value;

wherein the first parameter value differs from the second parameter value by at least one Just-Noticeable-Difference (JND) of the second type of sense of the subject.

The interface device 940 may also send the determined parameter values to an array of motors to cause the array of motors to generate tactile stimuli to a subject.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data streams along a local network or a publically accessible network such as the internet.

It should also be understood that, unless specifically stated otherwise as apparent from the following discussion, it is appreciated that throughout the description, discussions utilizing terms such as "receiving" or "obtaining" or "determining" or "sending" or "mapping" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The invention claimed is:

1. A method performed by a sensory substitution system for representing intensity levels indicative of a first type of sense of a subject by parameter values for a different second type of sense of the subject, the sensory substitution system comprising a processor and a sensory output device, the processor performing the method of:

determining a first parameter value for the second type of sense representing a first intensity level indicative of the first type of sense; and determining a second parameter value for the second type of sense representing a second intensity level indicative of the first type of sense with reference to the first parameter value;

wherein the first parameter value differs from the second parameter value by at least one Just-Noticeable-Difference (JND) of the second type of sense of the subject; and wherein the second parameter value is provided as input to a sensory output device.

2. The method according to claim 1, wherein determining the first parameter value for the second type of sense further comprises:

determining a plurality of parameter values for the second type of sense of the subject that are distinguishable to the subject based on JNDs of the second type of sense; and selecting one of the plurality of parameter values for the second type of sense being the first parameter value.

3. The method according to claim 2, wherein selecting the one of the plurality of parameter values comprises:

determining a value range of the intensity levels indicative of the first type of sense;

dividing the value range into a plurality of intervals based on JNDs of the first type of sense of the subject, wherein the number of the plurality of intervals is equal to the number of the plurality of parameter values for the second type of sense; and selecting, based on the plurality of intervals, the one of the plurality of parameter values for the second type of sense being the first parameter value.

4. The method according to claim 2, wherein the plurality of parameter values for the second type of sense comprises all parameter values for the second type of sense that are distinguishable to the subject.

5. The method according to claim 2, wherein determining the second parameter value for the second type of sense further comprises:

selecting another one of the plurality of parameter values for the second type of sense being the second parameter value.

6. The method according to claim 1, wherein the first type of sense comprises visual perception, auditory perception, ranging perception, gustatory perception, olfactory perception, vestibular perception.

7. The method according to claim 1, wherein the second type of sense comprises tactility and the parameter values for the second type of sense comprises electric voltage and electric current.

8. The method according to claim 1, wherein the first intensity level indicative of the first type of sense comprises a first visual intensity level indicative of a first portion of an image, and the second intensity level indicative of the first type of sense comprises a second visual intensity level indicative of a second portion of the same image.

9. The method according to claim 8, wherein the second portion of the image comprises at least part of a Region of Interest (ROI) of the image.

10. The method according to claim 9, wherein the ROI comprises a region in which the intensity levels change over time.

11. The method according to claim 9, wherein the ROI comprises a moving object in the image.

12. The method according to claim 9, wherein the ROI comprises an edge in the image.

13. The method according to claim 9, wherein the ROI comprises a scene object in the image.

14. The method according to claim 1, further comprising adjusting the parameter values for the second type of sense over time to counter adaptation to the second type of sense.

15. The method according to claim 1, wherein the first intensity level differs from the second intensity level by less than one JND of the first type of sense of the subject.

16. A non-transitory computer-readable medium, including computer-executable instructions stored thereon that when executed by a processor causes the processor to perform the method of claim 1.

17. A sensory substitution system for representing intensity levels indicative of a first type of sense of a subject by parameter values for a different second type of sense of the subject, the sensory substitution system comprising:
  a sensory output device; and
  a processor to perform the instructions from the memory communicated via the bus:
    to determine a first parameter value for the second type of sense representing a first intensity level indicative of the first type of sense; and
    to determine a second parameter value for the second type of sense representing a second intensity level indicative of the first type of sense with reference to the first parameter value;
    to provide the second parameter value as input to the sensory output device;
    wherein the first parameter value differs from the second parameter value by at least one Just-Noticeable-Difference (JND) of the second type of sense of the subject.

18. A sensory substitution system for translating intensity levels indicative of visual information to intensity levels indicative of tactile perception of a subject, comprising:
  a sensory information capture device to capture the intensity levels indicative of visual information of the subject;
  an array of stimulation generation members; and
  a processor
    to determine a first parameter value for tactile perception representing a first intensity level indicative of visual information; and
    to determine a second parameter value for tactile perception representing a second intensity level indicative of visual information with reference to the first parameter value;
    to provide the second parameter value as input to an array of stimulation generation members;
    wherein the first parameter value differs from the second parameter value by at least one Just-Noticeable-Difference (JND) of tactile perception of the subject.

19. The sensory substitution system according to claim 18, wherein the information capture device comprises a camera.

20. The sensory substitution system according to claim 18, wherein the sensory stimulation generation device comprises a coin motor or an electrode.

* * * * *